DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JANUARY 1, 1974

918 O.G. 104

T918,004

PROGRAM GENERATOR FOR BRANCHING QUESTIONNAIRE

William M. Chappell, Yorktown Heights, Hugh C. Fallon, Mohegan Lake, Gerald Geortzel, White Plains, and William G. Strohm, Yorktown Heights, N.Y., assignors to International Business Machines Corporation, Armonk, N.Y.

Continuation of application Ser. No. 213,909, Dec. 30, 1971. This application Apr. 3, 1973, Ser. No. 347,591

**Int. Cl. G06f *7/00***

U.S. Cl. 340—172.5

20 Sheets Drawing. 82 Pages Specification

Figure 1A:
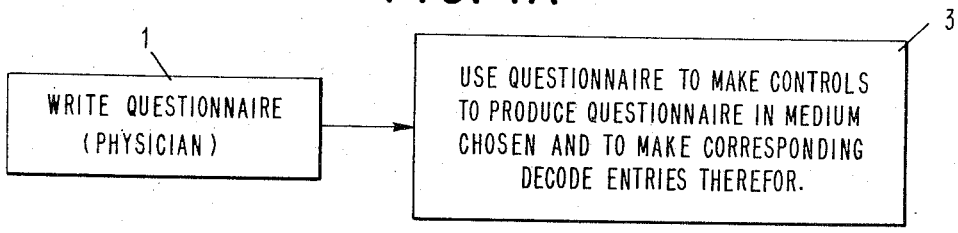
Figure 1B:
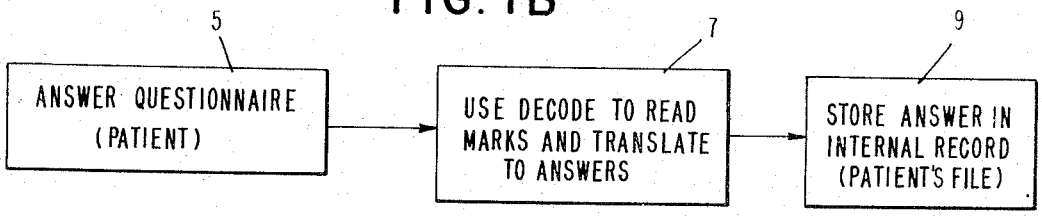
Figure 2:
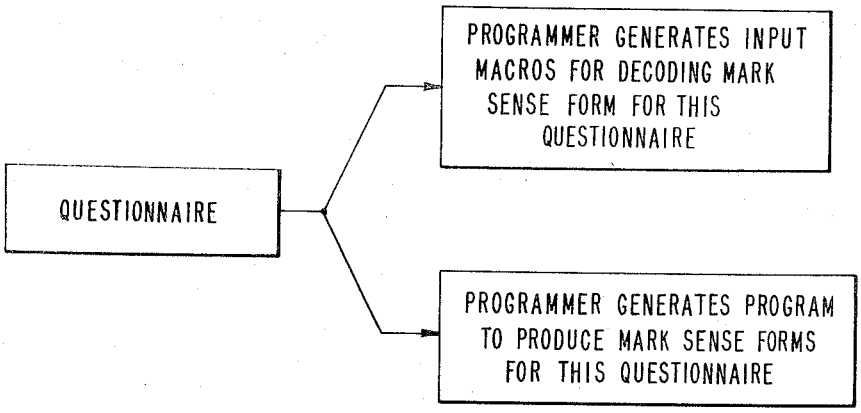
FIG. 2 (PRIOR ART)
Figure 3:
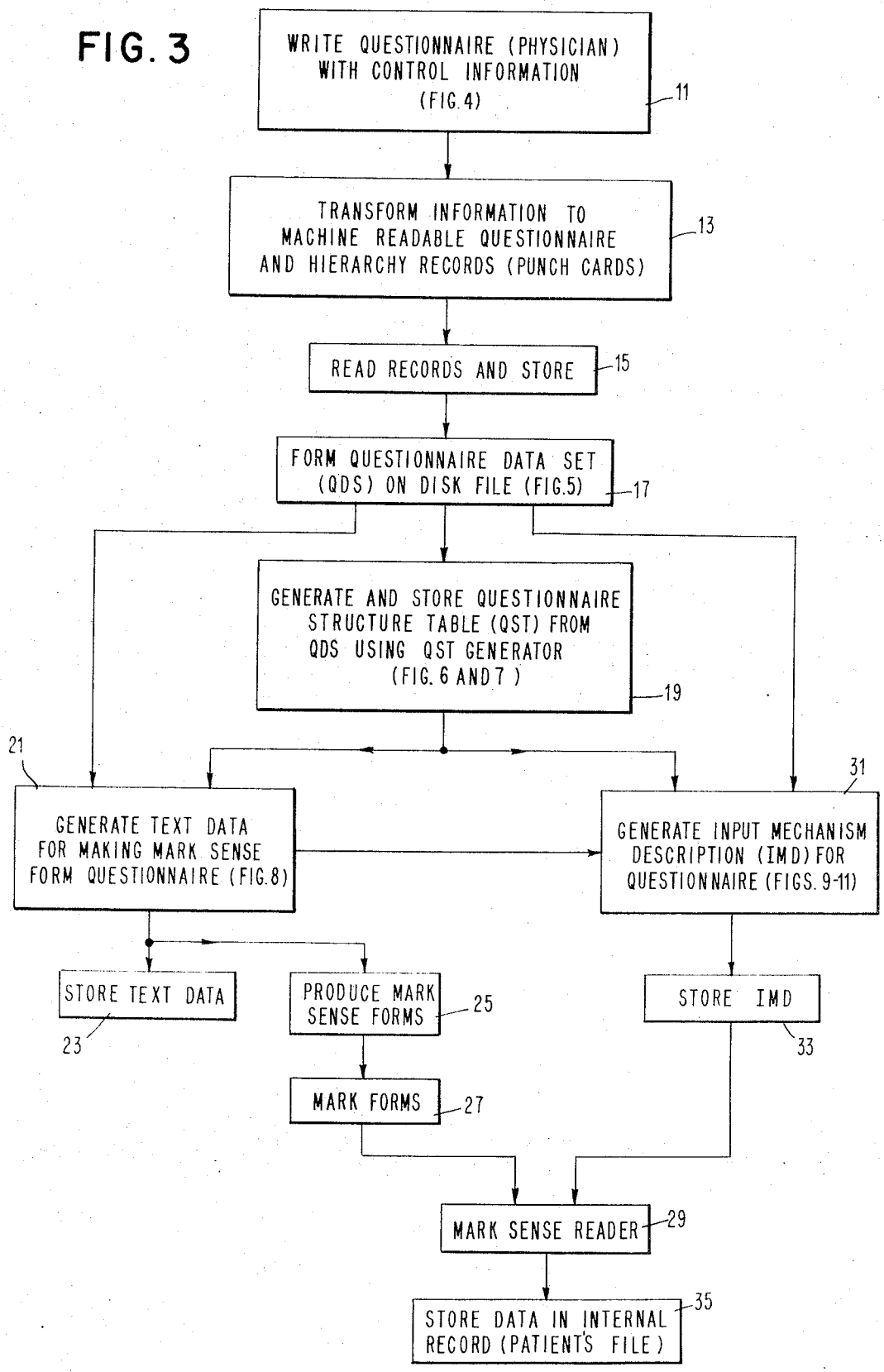
Figure 4:
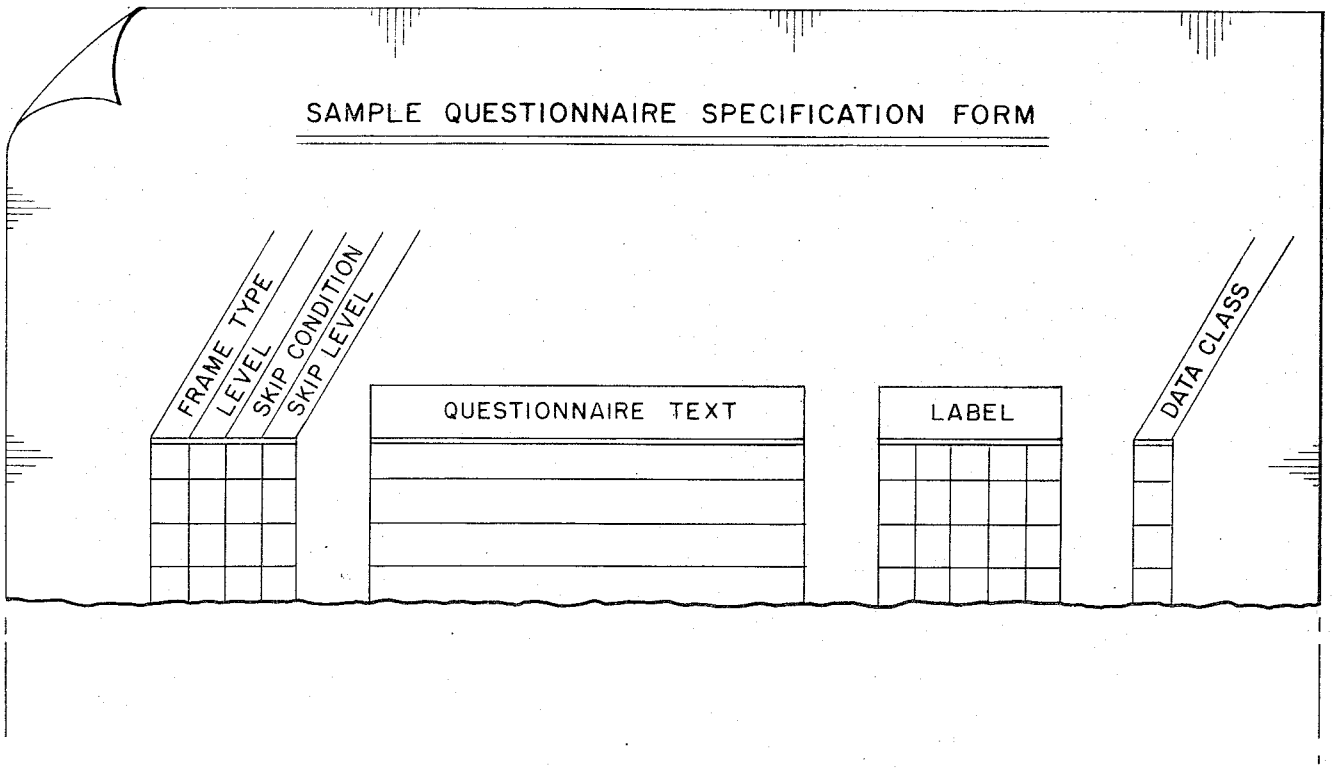
Figure 6A:
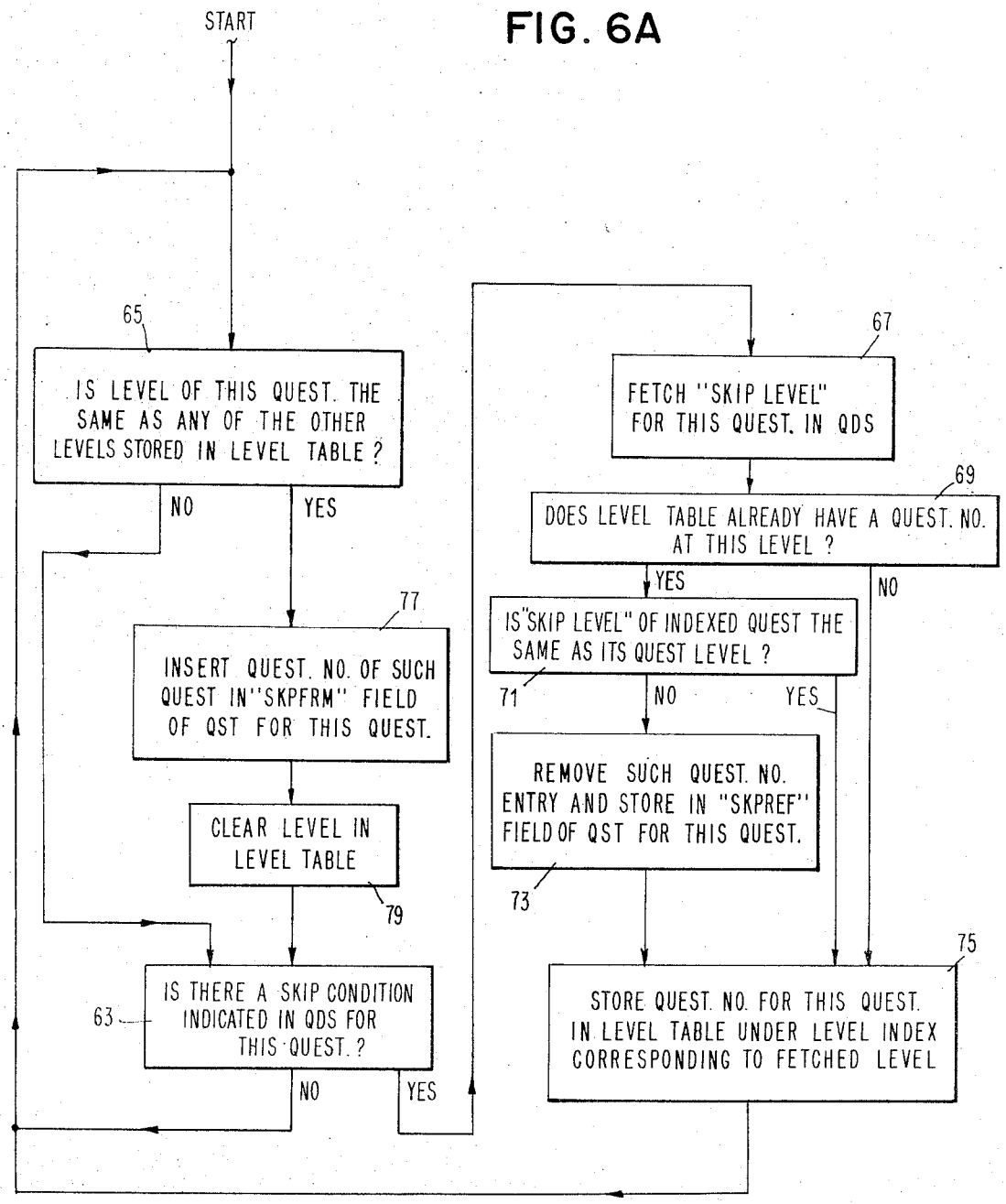
Figures 1, 6B:
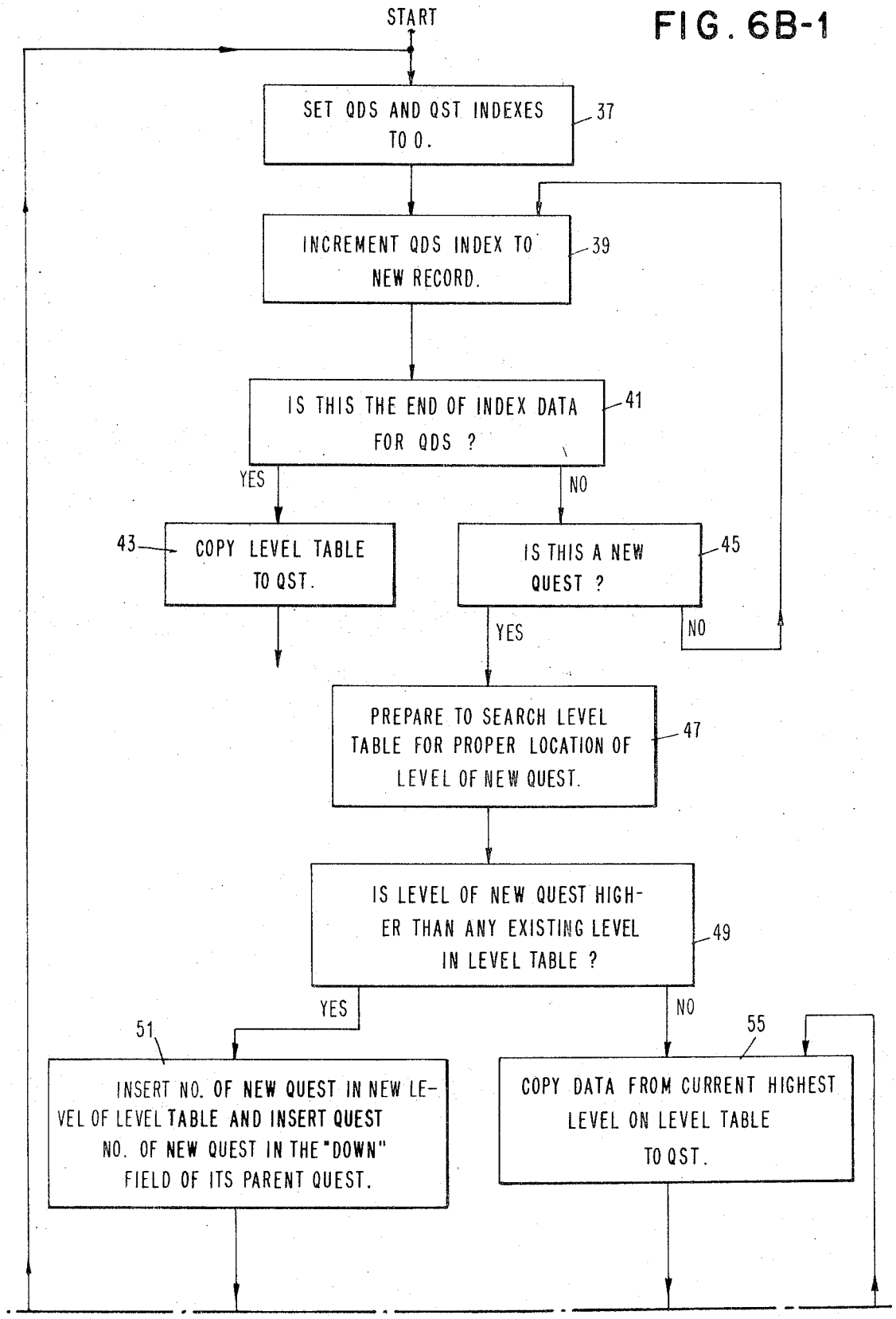
Figures 2, 6B:
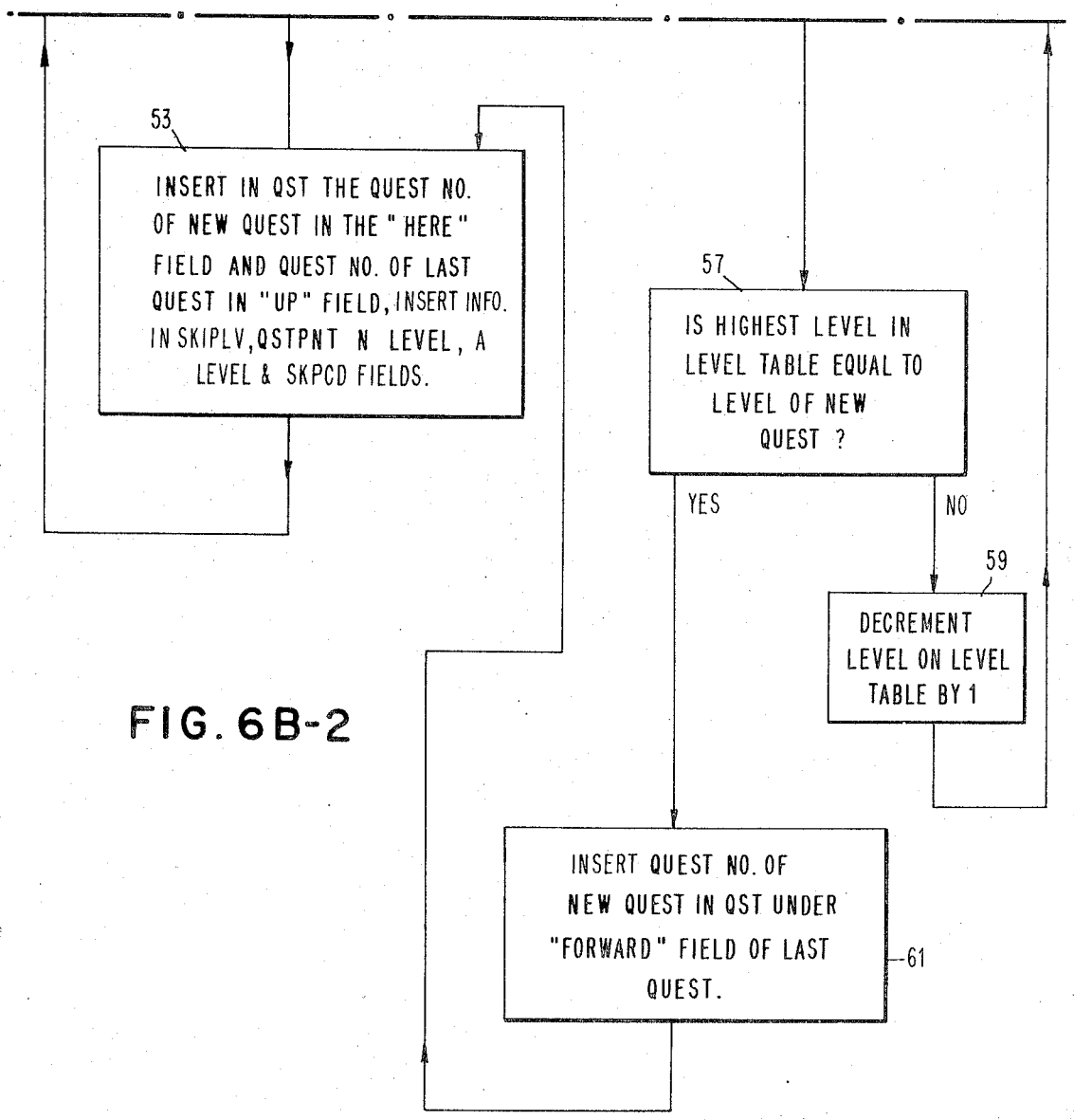
Figure 6B:
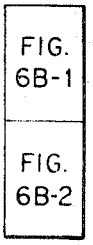
Figures 9, 9A, 9B, 9C:
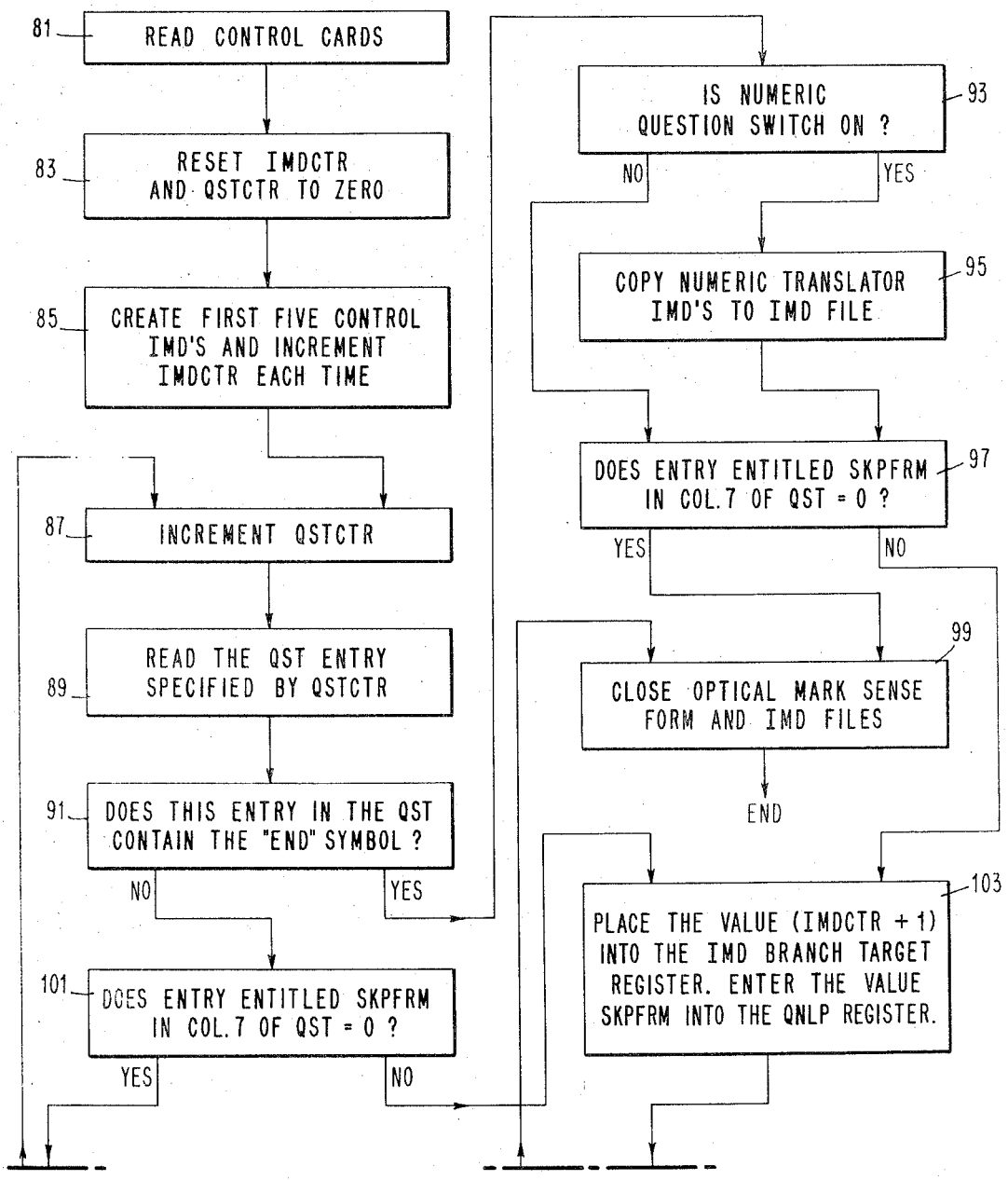
Figure 9B:
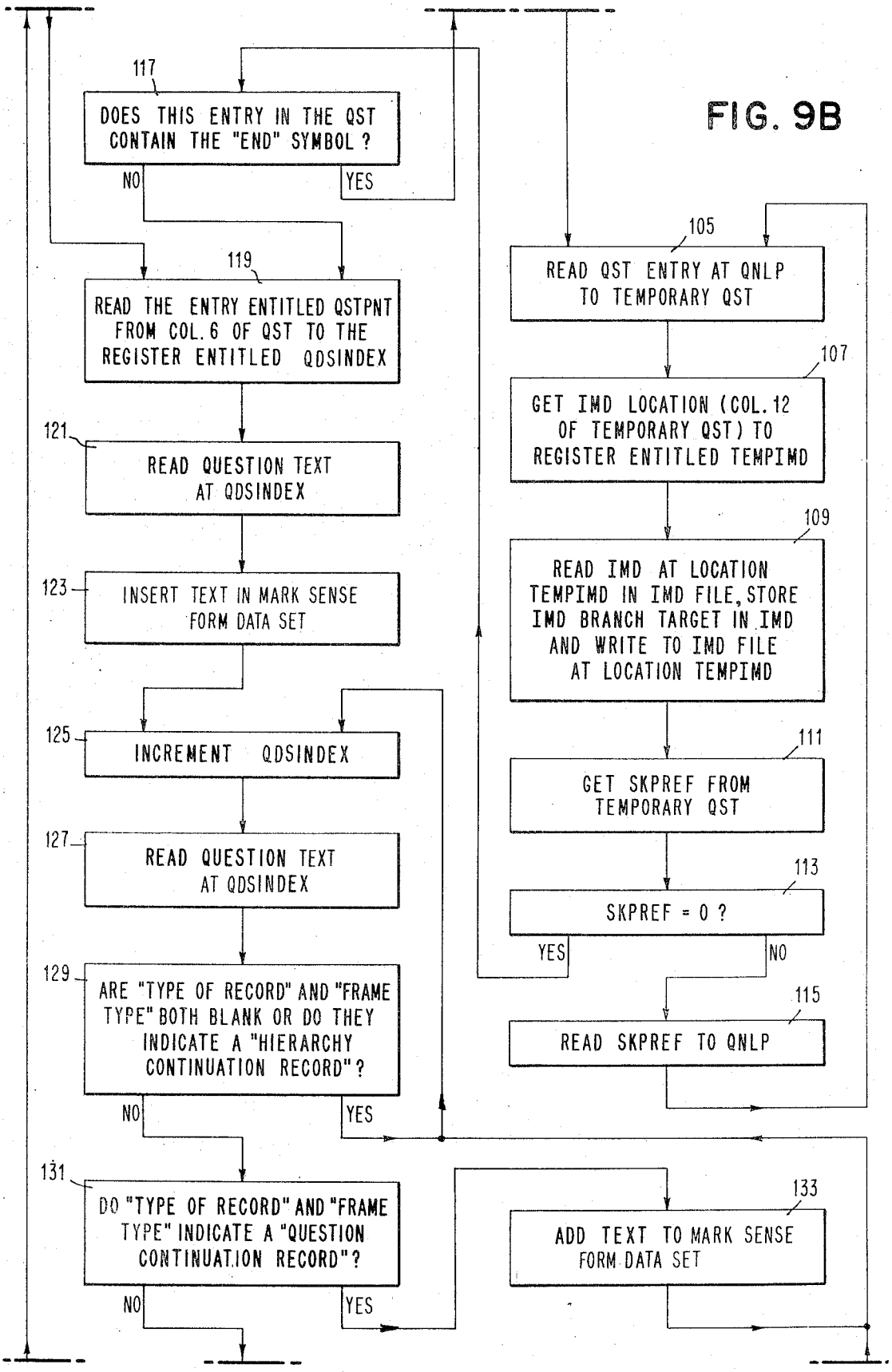
Figure 9C:
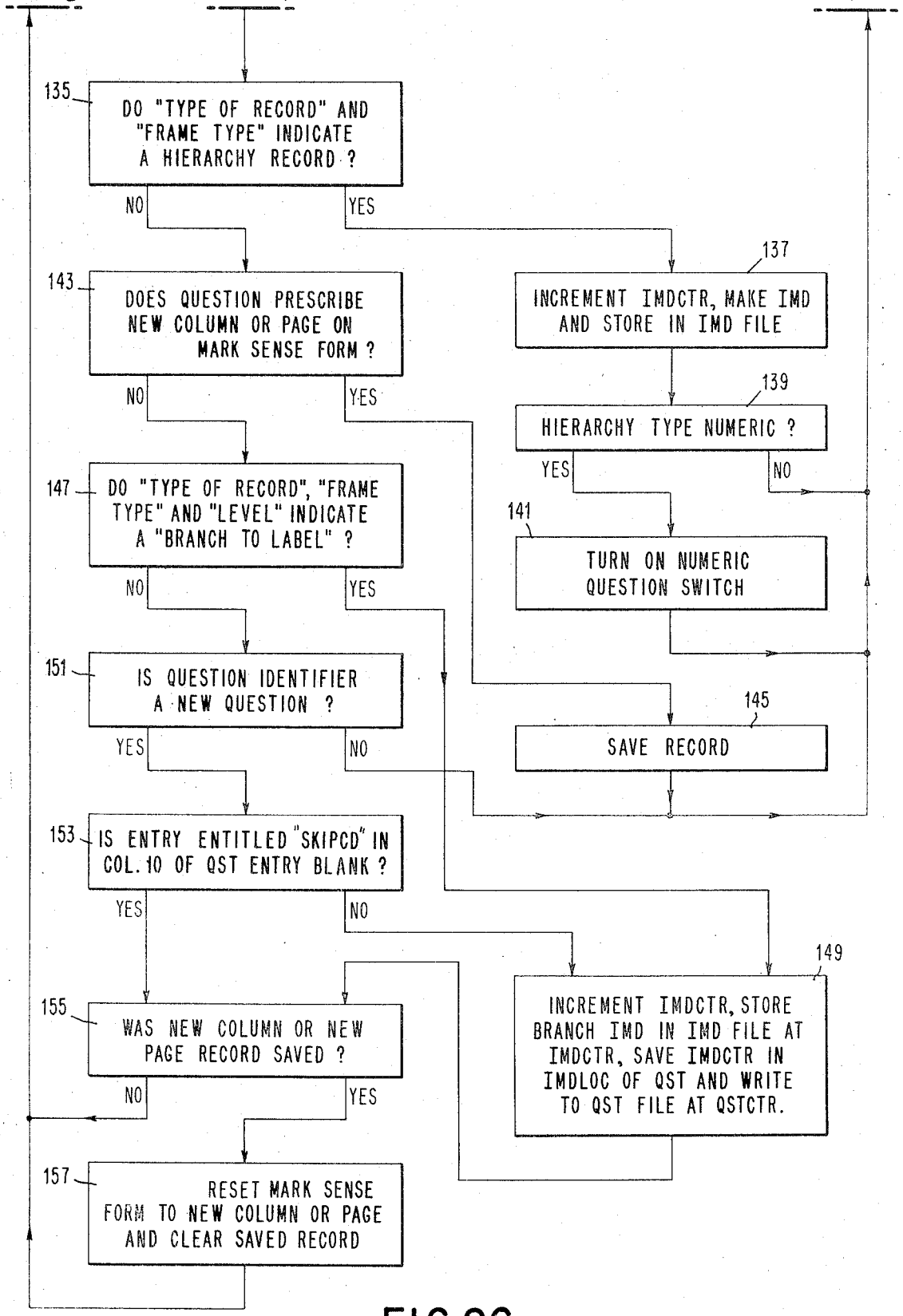

A computer system is provided, as represented by FIG. 3, for automatically generating, in response to a specified tree-structured branching questionnaire, the decode program instructions required by the computer to decode the responses to the respective queries of said questionnaire. The creator of the branching questionnaire specifies same, on a convenient form, via writing the basic information required by the computer to generate the data and programs for producing both the branching questionnaire text and decode program instructions therefor. After the basic information specified by the creator of the questionnaire, along with appropriate control information therefor, is entered into the computer, the computer automatically arranges same to form a questionnaire data set, which is stored on disk file as shown at 17. The questionnaire data set provides a conveniently addressable compilation of the information entered into the computer. The computer then acts to retrieve from the questionnaire data set, that information defined therein which is basically representative of the tree structure, and transforms this information into a questionnaire structure table as shown at 19, which table uniquely and unambiguously represents, in a particular tree form arrangement, the essential data required by the computer to automatically generate the decode program instructions. The questionnaire structure table and questionnaire data set are cooperatively employed by the computer to generate an image of the text of the queries of said questionnaire as shown at 21 and 23 and, in association with the position of the respective designated locations or spots in the text of said queries at which a manual response to each query is to be made, to generate at 31 the decode instructions (called IMD's) required by the computer to decode the responses thereto.

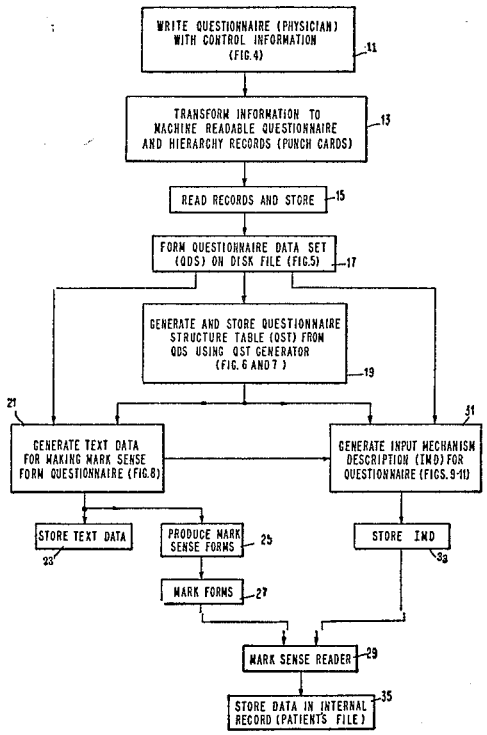

PROGRAM GENERATOR FOR BRANCHING QUESTIONNAIRE

Original Filed Dec. 30, 1971 20 Sheets-Sheet 1

INVENTORS
WILLIAM M. CHAPPELL
HUGH C. FALLON
GERALD GOERTZEL
WILLIAM G. STROHM

BY John A. Jordan
ATTORNEY

PROGRAM GENERATOR FOR BRANCHING QUESTIONNAIRE

Original Filed Dec. 30, 1971 20 Sheets-Sheet 2

| | | | | | | | | | |
|---|---|---|---|---|---|---|---|---|---|
| 31 | 14 | Q | S | C | | | | | OCCASIONALLY ? |
| 32 | | H | | | | | 1915 | | |
| 33 | 15 | Q | S | C | | | | | FREQUENTLY ? |
| 34 | | H | | | | | 1916 | | |
| 35 | 16 | Q | | C | | | | | HOW LONG DO YOUR ANXIETY PERIODS USUALLY LAST ? (IN HOURS) |
| 36 | | Q | * | | | | | | |
| 37 | | H | | | | | 999 | N2 | |
| 38 | 17 | Q | | C | | | | | WHAT WAS LOWEST REC'D. BODY TEMP ? |
| 39 | | H | | | | | LTEMP | N3.1 | |
| 40 | 18 | Q | S | C | N | B | | | CAN YOU DESCRIBE SYMPTOMS OF ANXIETY |
| 41 | | H | | | | | 1917 | | |
| 42 | 19 | Q | M | D | | | | | RESTLESSNESS |
| 43 | | H | | | | | 1918 | | |
| 44 | 20 | Q | M | D | | | | | WEAKNESS |
| 45 | | H | | | | | 1919 | | |
| 46 | 21 | Q | M | D | | | | | JITTERINESS |
| 47 | | H | | | | | 1920 | | |
| 48 | 22 | Q | M | D | | | | | IRRITABILITY |
| 49 | | H | | | | | 1921 | | |
| 50 | 23 | Q | M | D | | | | | CRYING |
| 51 | | H | | | | | 1922 | | |
| 52 | 24 | Q | F | B | | | | | WHAT IS YOUR SOCIAL SECURITY NO. ? |
| 53 | | Q | * | | | | | | 3(0····9) 2(0····9) 4(0····9) |
| 54 | | H | | | | | 999 | T | |
| 55 | 25 | Q | # | B | | | | | QUEST EXIT |
| 56 | | Q | F | | | | | | IF MALE, WHAT IS YOUR DRAFT STATUS ? |
| 57 | | Q | * | L | | | | | (12345)(ABCDFOSWY) |
| 58 | | H | | | | | 999 | T | |

FIG. 5B

FIG. 5

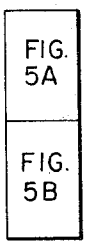

FIG. 5A

QUESTIONNAIRE DATA SET (QDS)

| RECORD NUMBER | QUESTION NUMBER | TYPE OF RECORD | FRAME TYPE | LEVEL | SKIP CONDITION | SKIP LEVEL | LABEL | DATA CLASS | QUESTION TEXT |
|---|---|---|---|---|---|---|---|---|---|
| 1 | 1 | Q | S | A | N | A | | | DO YOU WANT TO TAKE A PSYCHE EXAM ? |
| 2 | | H | | | | | 1902 | | |
| 3 | 2 | Q | S | B | | | | | HAVE YOU ANSWERED THIS QUESTIONNAIRE PREVIOUSLY ? |
| 4 | | Q | * | | | | | | |
| 5 | | Q | # | B | Y | | | | QUEST EXIT |
| 6 | | H | | | | | 999 | | |
| 7 | 3 | Q | S | B | N | B | | | BEEN DEPRESSED LATELY ? |
| 8 | | H | | | | | 1904 | | |
| 9 | | H | | | | | 1905 | | ** DUP. OF ABOVE NODE ** |
| 10 | 4 | Q | S | C | | | | | OCCASIONALLY ? |
| 11 | | H | | | | | 1906 | | |
| 12 | 5 | Q | S | C | | | | | FREQUENTLY ? |
| 13 | | H | | | | | 1907 | | |
| 14 | 6 | Q | | C | | | | | HOW LONG DO YOUR DEPRESSIVE PERIODS LAST ? (IN HOURS) |
| 15 | | Q | * | | | | | | |
| 16 | | H | | | | | 999 | N2 | |
| 17 | 7 | Q | | C | | | | | WHAT WAS HIGHEST REC'D. BODY TEMP ? |
| 18 | | H | | | | | HTEMP | N3.1 | |
| 19 | 8 | Q | E | D | Y | A | | | IS THIS EXAM DEPRESSING ? |
| 20 | | H | | | | | INVRT | I | |
| 21 | 9 | Q | S | C | N | B | | | CAN YOU DESCRIBE YOUR DEPRESSION ? |
| 22 | | H | | | | | 1908 | | |
| 23 | 10 | Q | M | D | | | | | NO PEP |
| 24 | | H | | | | | 1909 | | |
| 25 | 11 | Q | M | D | | | | | CRYING TENDENCY |
| 26 | | H | | | | | 1911 | | |
| 27 | 12 | Q | M | D | | | | | LACK OF INTEREST |
| 28 | | H | | | | | 1910 | | |
| 29 | 13 | Q | S | B | N | B | | | HAD ANXIETY LATELY ? |
| 30 | | H | | | | | 1913 | | |

PROGRAM GENERATOR FOR BRANCHING QUESTIONNAIRE

Original Filed Dec. 30, 1971 20 Sheets-Sheet 6

PROGRAM GENERATOR FOR BRANCHING QUESTIONNAIRE

Original Filed Dec. 30, 1971 20 Sheets-Sheet 7

PROGRAM GENERATOR FOR BRANCHING QUESTIONNAIRE

Original Filed Dec. 30, 1971 20 Sheets-Sheet 9

FIG. 7

QUESTIONNAIRE STRUCTURE TABLE (QST)

| "HERE" QUESTION NUMBER OF QUESTION IN THE QUESTIONNAIRE DATA SET. COL. 1 | "UP" QUESTION NUMBER OF MOST RECENT QUESTION IN THE QUESTIONAIRE DATA SET WITH HIGHER LEVEL THAN PRESENT QUESTION. COL. 2 | "DOWN" QUESTION NUMBER OF NEXT LOWER QUESTION IN THE QUESTIONAIRE DATA SET WHOSE UP POINTS TO PRESENT QUESTION. COL. 3 | "FORWARD" QUESTION NUMBER OF NEXT QUESTION IN THE QUESTIONAIRE DATA SET WITH THE SAME LEVEL AND SAME UP POINTER. COL. 4 | SKIPLV- LEVEL OF NEXT QUESTION IN THE QDS TO WHICH THIS QUESTION SPECIFIES IT SHOULD SKIP IF SUCH A SKIP CONDITION IS PRESENT. COL. 5 | QSTPNT- RECORD ADDRESS OF THIS QUESTION IN THE QUESTIONNAIRE DATA SET. COL. 6 | SKPFRM- QUESTION NUMBER OF QUESTION IN THE QUESTIONNAIRE DATA SET WHOSE SKIPLV POINTS TO THIS QUESTION. COL. 7 | SKPREF- QUESTION NUMBER OF A PREVIOUS QUESTION IN THE QUESTIONNAIRE DATA SET WHOSE SKIPLV IS SAME AS THIS QUESTION COL. 8 | N LEVEL- THE NUMERIC VALUE FOR THIS QUESTION'S LEVEL (i.e., A=1, B=2 etc.) COL. 9 | SKIPCD- CONDITION ON WHICH SKIPPING SHOULD OCCUR (i.e., Y=YES, N=NO) COL. 10 | A LEVEL- ALPHABETIC LEVEL OF THIS QUESTION IN THE QUESTIONNAIRE DATA SET. COL. 11 | IMD LOCATION COL. 12 |
|---|---|---|---|---|---|---|---|---|---|---|---|
| 1 | 0 | 2 | 26 | 1 | 1 | 0 | 0 | 1 | N | A | 8 |
| 2 | 1 | 0 | 3 | 0 | 3 | 0 | 0 | 2 | | B | 11 |
| 3 | 1 | 4 | 13 | 2 | 7 | 0 | 0 | 2 | N | B | 16 |
| 4 | 3 | 0 | 5 | 0 | 10 | 0 | 0 | 3 | | C | |
| 5 | 3 | 0 | 6 | 0 | 12 | 0 | 0 | 3 | | C | |
| 6 | 3 | 0 | 7 | 0 | 14 | 0 | 0 | 3 | | C | |
| 7 | 3 | 8 | 9 | 0 | 17 | 0 | 0 | 3 | | C | |
| 8 | 7 | 0 | 0 | A | 19 | 0 | 1 | 4 | Y | D | 24 |
| 9 | 3 | 10 | 0 | 2 | 21 | 0 | 3 | 3 | N | C | 27 |
| 10 | 9 | 0 | 11 | 0 | 23 | 0 | 0 | 4 | | D | |
| 11 | 9 | 0 | 12 | 0 | 25 | 0 | 0 | 4 | | D | |
| 12 | 9 | 0 | 0 | 0 | 27 | 0 | 0 | 4 | | D | |
| 13 | 1 | 14 | 24 | 2 | 29 | 9 | 0 | 2 | N | B | 33 |
| 14 | 13 | 0 | 15 | 0 | 31 | 0 | 0 | 3 | | C | |
| 15 | 13 | 0 | 16 | 0 | 33 | 0 | 0 | 3 | | C | |
| 16 | 13 | 0 | 17 | 0 | 35 | 0 | 0 | 3 | | C | |
| 17 | 13 | 0 | 18 | 0 | 38 | 0 | 0 | 3 | | C | |
| 18 | 13 | 19 | 0 | 2 | 40 | 0 | 13 | 3 | N | C | 42 |
| 19 | 18 | 0 | 20 | 0 | 42 | 0 | 0 | 4 | | D | |
| 20 | 18 | 0 | 21 | 0 | 44 | 0 | 0 | 4 | | D | |
| 21 | 18 | 0 | 22 | 0 | 46 | 0 | 0 | 4 | | D | |
| 22 | 18 | 0 | 23 | 0 | 48 | 0 | 0 | 4 | | D | |
| 23 | 18 | 0 | 0 | 0 | 50 | 0 | 0 | 4 | | D | |
| 24 | 1 | 0 | 25 | 0 | 52 | 18 | 0 | 2 | | B | |
| 25 | 1 | 0 | 0 | 0 | 55 | 2 | 0 | 2 | | B | |
| 26 | END SIGNAL | | | | | 8 | | | | | |

FIG. 8

SAMPLE QUESTIONNAIRE

NAME _____ DATE _____

YES NO ( ) A DO YOU WANT TO TAKE A PSYCHE EXAM ?

IF NO, DO NOT ANSWER REMAINING QUESTIONS ( ) B HAVE YOU ANSWERED THIS QUESTIONNAIRE PREVIOUSLY ?

IF YES, BRANCH TO: QUEST EXIT ( ) B BEEN DEPRESSED LATELY ?

IF NO, SKIP TO NEXT B.

( ) C OCCASIONALLY ?

( ) C FREQUENTLY ?

C HOW LONG DO YOUR DEPRESSIVE PERIODS LAST (IN HOURS) ?

> 0 1 2 3 4 5 6 7 8 9

> 0 1 2 3 4 5 6 7 8 9

>>> QUEST EXIT

B IF MALE, WHAT IS YOUR DRAFT STATUS ?

> 1 2 3 4 5

> A B C D F O S W Y

PROGRAM GENERATOR FOR BRANCHING QUESTIONNAIRE

Original Filed Dec. 30, 1971 20 Sheets-Sheet 13

FIG. 10A

INPUT MECHANISM DESCRIPTION (IMD)

| IMD NUMBER | IMD TYPE | GROUPING INDICATOR | QUESTION TYPE | IMD FOR BEGINNING OF TABLE | MARK SENSE FORM POSITION | | | QUESTION NUMBER | QUESTION VALUE | LABEL - REFERENCE TO PATIENT'S FILE | VALUE STORED IN PATIENT'S FILE | MARK SENSE POSITION FOR NUMERIC FIELD BEGINNING | | | MARK SENSE POSITION FOR NUMERIC FIELD END | | | TYPE OF NUMERIC | BRANCH QUESTION NUMBER | BRANCH QUESTION VALUE | BRANCH TARGET IMD NUMBER |
|---|---|---|---|---|---|---|---|---|---|---|---|---|---|---|---|---|---|---|---|---|---|
| | | | | | PAGE | ROW | COLUMN | | | | | PAGE | ROW | COLUMN | PAGE | ROW | COLUMN | | | | |
| 6 | T | / | B | 0 | 1 | 3 | 1 | 1 | Y | 1902 | Y | | | | | | | | | | |
| 7 | T | ) | B | 0 | 1 | 3 | 2 | 1 | N | 1902 | N | | | | | | | | | | |
| 8 | b | | | | | | | | | | | | | | | | | | 1 | N | 227 |
| 9 | T | / | B | 0 | 1 | 7 | 1 | 2 | Y | 999 | Y | | | | | | | | | | |
| 10 | T | ) | B | 0 | 1 | 7 | 2 | 2 | N | 999 | N | | | | | | | | | | |
| 11 | b | | | | | | | | | | | | | | | | | | 2 | Y | 50 |
| 12 | T | / | B | 0 | 1 | 11 | 1 | 3 | Y | 1904 | Y | | | | | | | | | | |
| 13 | T | ) | B | 0 | 1 | 11 | 2 | 3 | N | 1904 | N | | | | | | | | | | |
| 14 | T | / | B | 0 | 1 | 11 | 1 | 3 | Y | 1905 | Y | | | | | | | | | | |
| 15 | T | ) | B | 0 | 1 | 11 | 2 | 3 | N | 1905 | N | | | | | | | | | | |
| 16 | b | | | | | | | | | | | | | | | | | | 3 | N | 31 |
| 17 | T | / | B | 0 | 1 | 13 | 1 | 4 | Y | 1906 | Y | | | | | | | | | | |
| 18 | T | ) | B | 0 | 1 | 13 | 2 | 4 | N | 1906 | N | | | | | | | | | | |
| 19 | T | / | B | 0 | 1 | 14 | 1 | 5 | Y | 1907 | Y | | | | | | | | | | |
| 20 | T | ) | B | 0 | 1 | 14 | 2 | 5 | N | 1907 | N | | | | | | | | | | |
| 21 | T | | N | 51 | | | | 6 | Y | 999 | | 1 | 19 | 1 | 1 | 18 | 10 | 0 | | | |
| 22 | T | | N | 81 | | | | 7 | Y | HTEMP | | 1 | 26 | 1 | 1 | 23 | 10 | 1 | | | |
| 23 | T | | B | 0 | 1 | 29 | 1 | 8 | Y | INVRT | N | | | | | | | | | | |
| 24 | b | | | | | | | | | | | | | | | | | | 8 | Y | 227 |
| 25 | T | / | B | 0 | 1 | 33 | 1 | 9 | Y | 1908 | Y | | | | | | | | | | |
| 26 | T | ) | B | 0 | 1 | 33 | 2 | 9 | N | 1908 | N | | | | | | | | | | |
| 27 | b | | | | | | | | | | | | | | | | | | 9 | N | 31 |

| | | | | | | | | | | | | | | | | | | |
|---|---|---|---|---|---|---|---|---|---|---|---|---|---|---|---|---|---|---|
| 28 T B | 0 | 1 | 36 | 1 | 10 | Y | 1909 | Y | | | | | | | | | | |
| 29 T B | 0 | 1 | 37 | 1 | 11 | Y | 1911 | Y | | | | | | | | | | |
| 30 T B | 0 | 1 | 3 | 11 | 12 | Y | 1910 | Y | | | | | | | | | | |
| 31 T / B | 0 | 1 | 5 | 11 | 13 | Y | 1913 | Y | | | | | | | | | | |
| 32 T ) B | 0 | 1 | 5 | 12 | 13 | N | 1913 | N | | | | | | | | | | |
| 33 b | | | | | | | | | | | | | | | | 13 | N | 48 |
| 34 T / B | 0 | 1 | 7 | 11 | 14 | Y | 1915 | Y | | | | | | | | | | |
| 35 T ) B | 0 | 1 | 7 | 12 | 14 | N | 1915 | N | | | | | | | | | | |
| 36 T / B | 0 | 1 | 8 | 11 | 15 | Y | 1916 | Y | | | | | | | | | | |
| 37 T ) B | 0 | 1 | 8 | 12 | 15 | N | 1916 | N | | | | | | | | | | |
| 38 T N | 51 | | | | 16 | Y | 999 | | 1 | 13 | 11 | 1 | 12 | 20 | 0 | | | |
| 39 T N | 81 | | | | 17 | Y | LTEMP | | 1 | 20 | 11 | 1 | 17 | 20 | 1 | | | |
| 40 T / B | 0 | 1 | 23 | 11 | 18 | Y | 1917 | Y | | | | | | | | | | |
| 41 T ) B | 0 | 1 | 23 | 12 | 18 | N | 1917 | N | | | | | | | | | | |
| 42 b | | | | | | | | | | | | | | | | 18 | N | 48 |
| 43 T B | 0 | 1 | 26 | 11 | 19 | Y | 1918 | Y | | | | | | | | | | |
| 44 T B | 0 | 1 | 27 | 11 | 20 | Y | 1919 | Y | | | | | | | | | | |
| 45 T B | 0 | 1 | 28 | 11 | 21 | Y | 1920 | Y | | | | | | | | | | |
| 46 T B | 0 | 1 | 29 | 11 | 22 | Y | 1921 | Y | | | | | | | | | | |
| 47 T B | 0 | 1 | 30 | 11 | 23 | Y | 1922 | Y | | | | | | | | | | |
| | CONTROL IMD FOR PAGE 2 | | | | | | | | | | | | | | | | | |
| 49 T t | 135 | | | | 24 | | 999 | | 2 | 3 | 1 | 2 | 11 | 10 | 0 | | | |
| 50 T t | 121 | | | | 25 | | 999 | | 2 | 18 | 1 | 2 | 19 | 10 | 0 | | | |

NOTE: IN "IMD TYPE" COLUMN, T = TRANSLATE, b = BRANCH

IN "GROUPING INDICATOR" COLUMN,

/ = BEGINNING OF A GROUP OF IMD'S WHICH IS EXCLUSIVE - EXCLUSIVE MEANS THAT AT MOST, ONLY ONE MARK SHOULD BE MADE.

( = BEGINNING OF A GROUP OF IMD'S WHICH IS REQUIRED - REQUIRED MEANS THAT AT LEAST ONE MARK MUST BE MADE BUT THAT THERE CAN BE MORE THAN ONE MARK MADE.

) = END OF ANY GROUP

IN "QUESTION TYPE" COLUMN,

B = BOOLEAN, N = NUMERIC, t = TEXT

FIG. 10B

FIG. 10

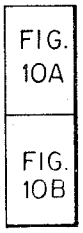

FIG. 11A

TABLE VALUE IMD

| IMD # — IMD TYPE — GROUPING INDICATOR FOR TABLE | ROW OFFSET IN TABLE | COLUMN OFFSET IN TABLE | VALUE TO BE POSTED TO REGISTER / OR SHIFTER |
|---|---|---|---|
| 51 V | 0 | 0 | 0.00000 |
| 52 V | 0 | 1 | 1.00000 |
| 53 V | 0 | 2 | 2.00000 |
| 54 V | 0 | 3 | 3.00000 |
| 55 V | 0 | 4 | 4.00000 |
| 56 V | 0 | 5 | 5.00000 |
| 57 V | 0 | 6 | 6.00000 |
| 58 V | 0 | 7 | 7.00000 |
| 59 V | 0 | 8 | 8.00000 |
| 60 V * | 0 | 9 | 9.00000 |
| 61 V | −1 | 0 | 0.00000 |
| 62 V | −1 | 1 | 10.00000 |
| 63 V | −1 | 2 | 20.00000 |
| 64 V | −1 | 3 | 30.00000 |
| 65 V | −1 | 4 | 40.00000 |
| 66 V | −1 | 5 | 50.00000 |
| 67 V | −1 | 6 | 60.00000 |
| 68 V | −1 | 7 | 70.00000 |
| 69 V | −1 | 8 | 80.00000 |
| 70 V * | −1 | 9 | 90.00000 |
| 71 V | −2 | 0 | 0.00000 |
| 72 V | −2 | 1 | 100.00000 |
| 73 V | −2 | 2 | 200.00000 |
| 74 V | −2 | 3 | 300.00000 |
| 75 V | −2 | 4 | 400.00000 |
| 76 V | −2 | 5 | 500.00000 |
| 77 V | −2 | 6 | 600.00000 |
| 78 V | −2 | 7 | 700.00000 |
| 79 V | −2 | 8 | 800.00000 |
| 80 V * * | −2 | 9 | 900.00000 |
| 81 V | 0 | 0 | 0.00000 |
| 82 V | 0 | 1 | 0.10000 |
| 83 V | 0 | 2 | 0.20000 |

FIG. 11

FIG. 11A
FIG. 11B
FIG. 11C
FIG. 11D
FIG. 11E

| | | | | |
|---|---|---|---|---|
| 84 V | 0 | 3 | 0.30000 | |
| 85 V | 0 | 4 | 0.40000 | |
| 86 V | 0 | 5 | 0.50000 | |
| 87 V | 0 | 6 | 0.60000 | |
| 88 V | 0 | 7 | 0.70000 | |
| 89 V | 0 | 8 | 0.80000 | |
| 90 V * | 0 | 9 | 0.90000 | |
| 91 V | −1 | 0 | 0.00000 | |
| 92 V | −1 | 1 | 1.00000 | |
| 93 V | −1 | 2 | 2.00000 | |
| 94 V | −1 | 3 | 3.00000 | |
| 95 V | −1 | 4 | 4.00000 | |
| 96 V | −1 | 5 | 5.00000 | |
| 97 V | −1 | 6 | 6.00000 | |
| 98 V | −1 | 7 | 7.00000 | |
| 99 V | −1 | 8 | 8.00000 | |
| 100 V * | −1 | 9 | 9.00000 | |
| 101 V | −2 | 0 | 0.00000 | |
| 102 V | −2 | 1 | 10.00000 | |
| 103 V | −2 | 2 | 20.00000 | |
| 104 V | −2 | 3 | 30.00000 | |
| 105 V | −2 | 4 | 40.00000 | |
| 106 V | −2 | 5 | 50.00000 | |
| 107 V | −2 | 6 | 60.00000 | |
| 108 V | −2 | 7 | 70.00000 | |
| 109 V | −2 | 8 | 80.00000 | |
| 110 V * | −2 | 9 | 90.00000 | |
| 111 V | −3 | 0 | 0.00000 | |
| 112 V | −3 | 1 | 100.00000 | |
| 113 V | −3 | 2 | 200.00000 | |
| 114 V | −3 | 3 | 300.00000 | |
| 115 V | −3 | 4 | 400.00000 | |
| 116 V | −3 | 5 | 500.00000 | |
| 117 V | −3 | 6 | 600.00000 | END OF REGISTER VALUES |
| 118 V | −3 | 7 | 700.00000 | |
| 119 V | −3 | 8 | 800.00000 | |
| 120 V ** | −3 | 9 | 900.00000 | |
| 121 V | 0 | 0 | 1 | BEGINNING OF SHIFTER VALUES |
| 122 V | 0 | 1 | 2 | |
| 123 V | 0 | 2 | 3 | |
| 124 V | 0 | 3 | 4 | |
| 125 V * | 0 | 4 | 5 | |
| 126 V | 1 | 0 | A | |

FIG. 11B

| | | | |
|---|---|---|---|
| 127 V | 1 | 1 | B |
| 128 V | 1 | 2 | C |
| 129 V | 1 | 3 | D |
| 130 V | 1 | 4 | F |
| 131 V | 1 | 5 | 0 |
| 132 V | 1 | 6 | S |
| 133 V | 1 | 7 | W |
| 134 V ** | 1 | 8 | Y |
| 135 V | 0 | 0 | 0 |
| 136 V | 0 | 1 | 1 |
| 137 V | 0 | 2 | 2 |
| 138 V | 0 | 3 | 3 |
| 139 V | 0 | 4 | 4 |
| 140 V | 0 | 5 | 5 |
| 141 V | 0 | 6 | 6 |
| 142 V | 0 | 7 | 7 |
| 143 V | 0 | 8 | 8 |
| 144 V * | 0 | 9 | 9 |
| 145 V | 1 | 0 | 0 |
| 146 V | 1 | 1 | 1 |
| 147 V | 1 | 2 | 2 |
| 148 V | 1 | 3 | 3 |
| 149 V | 1 | 4 | 4 |
| 150 V | 1 | 5 | 5 |
| 151 V | 1 | 6 | 6 |
| 152 V | 1 | 7 | 7 |
| 153 V | 1 | 8 | 8 |
| 154 V | 1 | 9 | 9 |
| 155 V | 2 | 0 | 0 |
| 156 V | 2 | 1 | 1 |
| 157 V | 2 | 2 | 2 |
| 158 V | 2 | 3 | 3 |
| 159 V | 2 | 4 | 4 |
| 160 V | 2 | 5 | 5 |
| 161 V | 2 | 6 | 6 |
| 162 V | 2 | 7 | 7 |
| 163 V | 2 | 8 | 8 |
| 164 V * | 2 | 9 | 9 |
| 165 V * | 3 | 0 | |
| 166 V | 4 | 0 | 0 |

FIG. 11C

| | | | |
|---|---|---|---|
| 167 V | 4 | 1 | 1 |
| 168 V | 4 | 2 | 2 |
| 169 V | 4 | 3 | 3 |
| 170 V | 4 | 4 | 4 |
| 171 V | 4 | 5 | 5 |
| 172 V | 4 | 6 | 6 |
| 173 V | 4 | 7 | 7 |
| 174 V | 4 | 8 | 8 |
| 175 V * | 4 | 9 | 9 |
| 176 V | 5 | 0 | 0 |
| 177 V | 5 | 1 | 1 |
| 178 V | 5 | 2 | 2 |
| 179 V | 5 | 3 | 3 |
| 180 V | 5 | 4 | 4 |
| 181 V | 5 | 5 | 5 |
| 182 V | 5 | 6 | 6 |
| 183 V | 5 | 7 | 7 |
| 184 V | 5 | 8 | 8 |
| 185 V * | 5 | 9 | 9 |
| 186 V * | 6 | 0 | |
| 187 V | 7 | 0 | 0 |
| 188 V | 7 | 1 | 1 |
| 189 V | 7 | 2 | 2 |
| 190 V | 7 | 3 | 3 |
| 191 V | 7 | 4 | 4 |
| 192 V | 7 | 5 | 5 |
| 193 V | 7 | 6 | 6 |
| 194 V | 7 | 7 | 7 |
| 195 V | 7 | 8 | 8 |
| 196 V * | 7 | 9 | 9 |
| 197 V | 8 | 0 | 0 |
| 198 V | 8 | 1 | 1 |
| 199 V | 8 | 2 | 2 |
| 200 V | 8 | 3 | 3 |
| 201 V | 8 | 4 | 4 |
| 202 V | 8 | 5 | 5 |
| 203 V | 8 | 6 | 6 |
| 204 V | 8 | 7 | 7 |
| 205 V | 8 | 8 | 8 |
| 206 V * | 8 | 9 | 9 |

FIG. 11D

| | | | |
|---|---|---|---|
| 207 V | 9 | 0 | 0 |
| 208 V | 9 | 1 | 1 |
| 209 V | 9 | 2 | 2 |
| 210 V | 9 | 3 | 3 |
| 211 V | 9 | 4 | 4 |
| 212 V | 9 | 5 | 5 |
| 213 V | 9 | 6 | 6 |
| 214 V | 9 | 7 | 7 |
| 215 V | 9 | 8 | 8 |
| 216 V * | 9 | 9 | 9 |
| 217 V | 10 | 0 | 0 |
| 218 V | 10 | 1 | 1 |
| 219 V | 10 | 2 | 2 |
| 220 V | 10 | 3 | 3 |
| 221 V | 10 | 4 | 4 |
| 222 V | 10 | 5 | 5 |
| 223 V | 10 | 6 | 6 |
| 224 V | 10 | 7 | 7 |
| 225 V | 10 | 8 | 8 |
| 226 V ** | 10 | 9 | 9 |
| 227 * | "END" | | |

FIG. 11E